United States Patent [19]
Miller

[11] Patent Number: 5,104,623
[45] Date of Patent: Apr. 14, 1992

[54] APPARATUS AND ASSEMBLY FOR USE IN OPTICALLY SENSING A COMPOSITIONAL BLOOD PARAMETER

[75] Inventor: William W. Miller, Santa Ana, Calif.

[73] Assignee: Minnesota Mining and Manufacturing Company, St. Paul, Minn.

[21] Appl. No.: 504,123

[22] Filed: Apr. 3, 1990

[51] Int. Cl.⁵ .................. G01N 21/00; A61B 5/00
[52] U.S. Cl. .................. 422/82.06; 422/82.04; 436/68; 128/633
[58] Field of Search ............ 422/82.06; 128/633, 128/634; 436/68

[56] References Cited

U.S. PATENT DOCUMENTS

| | | | |
|---|---|---|---|
| 4,033,330 | 7/1977 | Willis et al. | 128/633 |
| 4,512,630 | 4/1985 | Runge | 350/96.21 |
| 4,640,820 | 2/1987 | Cooper | 422/82.04 |
| 4,737,343 | 4/1988 | Hirschfeld | 128/633 |
| 4,791,932 | 12/1988 | Margules | 128/633 |
| 4,830,013 | 5/1989 | Maxwell | 128/637 |
| 4,930,506 | 6/1990 | Ullrich | 128/633 |
| 4,973,561 | 11/1990 | Hansen et al. | 422/83 |

OTHER PUBLICATIONS

"Oxygen Saturation Monitor" (date, author unavailable).

Primary Examiner—Robert J. Warden
Assistant Examiner—Theresa A. Trembley
Attorney, Agent, or Firm—Gary L. Griswold; Walter N. Kirn; Dale E. Hulse

[57] ABSTRACT

An apparatus comprising a supporting structure having a surface, an optical sensor for sensing a compositional blood parameter and a deformable optical coupling element carried by the supporting structure. The optical sensor is carried by the supporting structure and is responsive to an optical input signal to provide an optical output signal related to the compositional blood parameter. The optical coupling element is in a position to receive at least one of the optical signals and the optical coupling element is transmissive to such received signal.

21 Claims, 3 Drawing Sheets

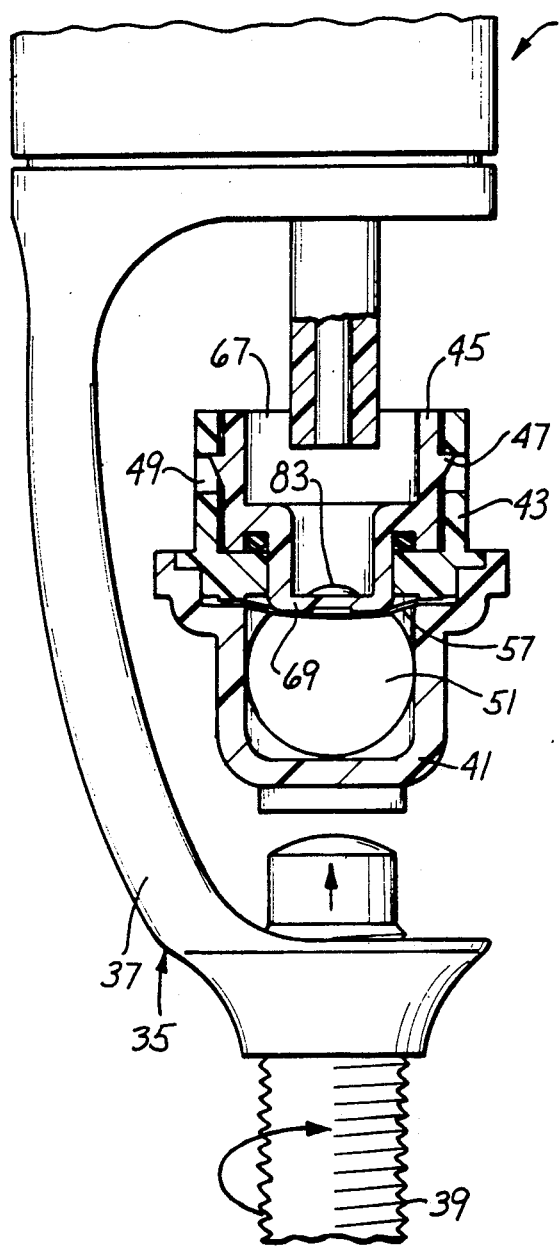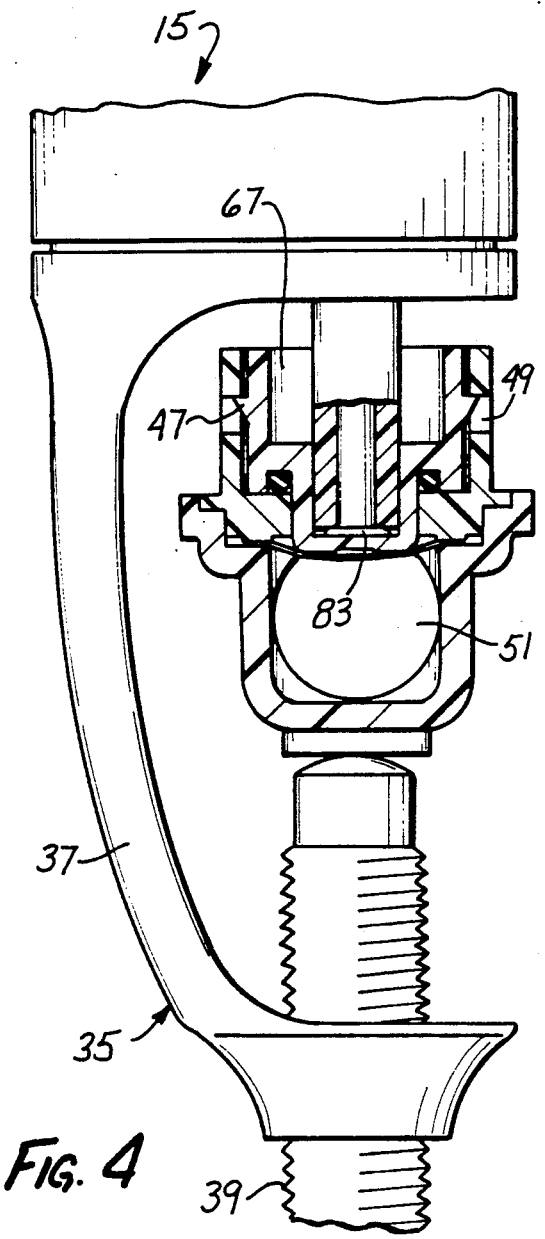

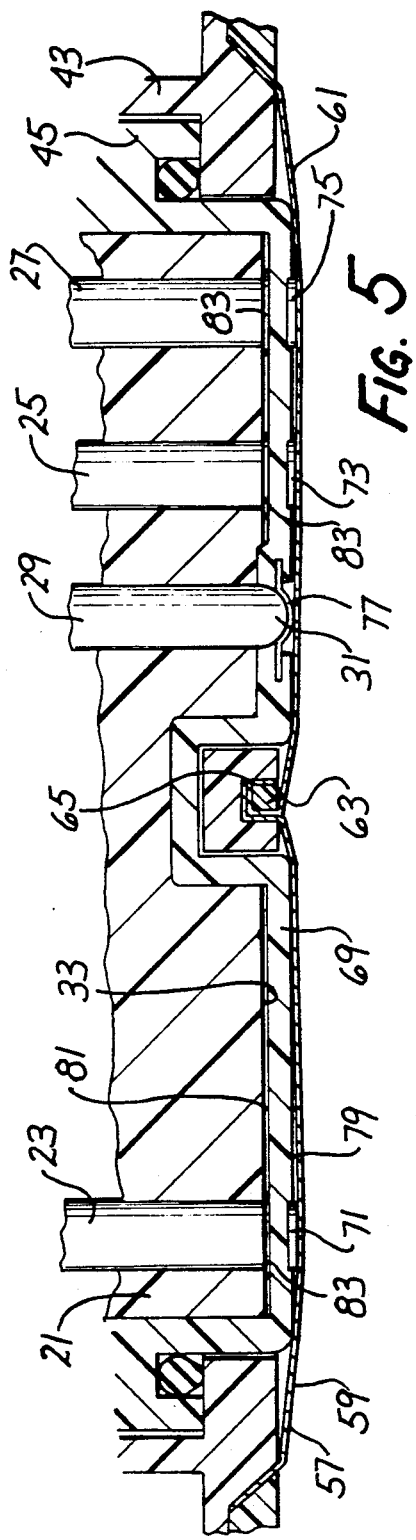
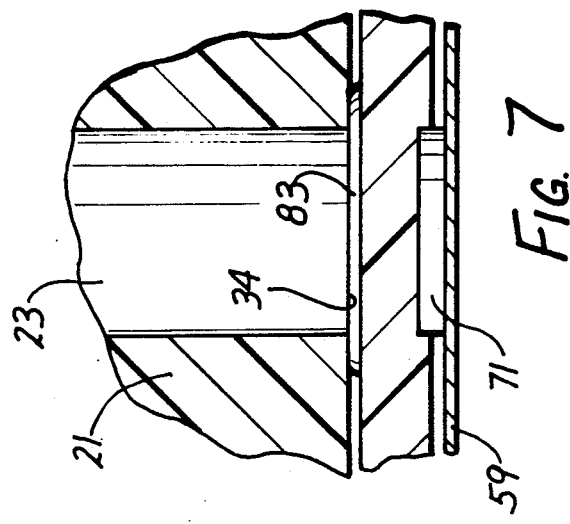
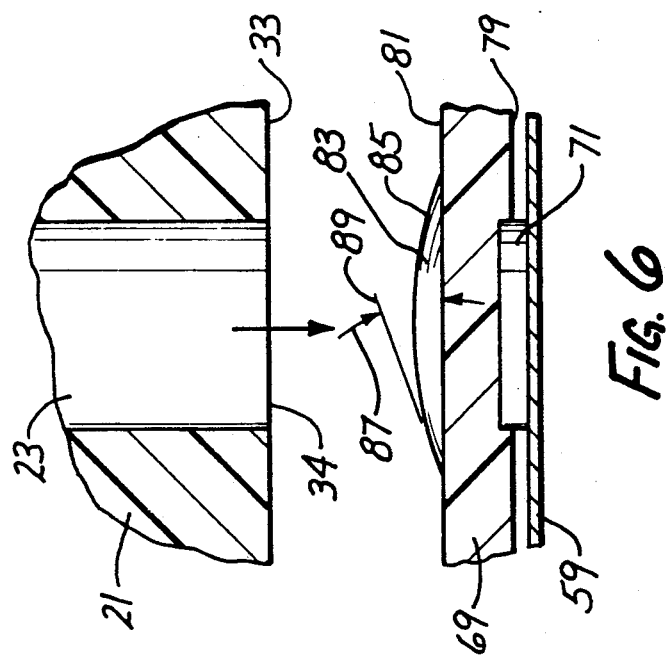

APPARATUS AND ASSEMBLY FOR USE IN OPTICALLY SENSING A COMPOSITIONAL BLOOD PARAMETER

BACKGROUND OF THE INVENTION

It is sometimes necessary or desirable to sense one or more of a variety of compositional blood parameters. Examples of such compositional blood parameters include the presence and/or concentration of blood constituents, such as blood gases, hydrogen ions (pH), other electrolytes, glucose, red blood cells and the like. Blood parameters can be sensed and appropriate measurements taken in real time, and this may be accomplished in vivo as set forth for example in Maxwell U.S. Pat. No. 4,830,013, in vitro or in an extracorporeal blood loop as disclosed in Cooper U.S. Pat. No. 4,640,820.

Many blood parameters of interest can advantageously be sensed optically and this can be accomplished, for example, using fluorescent, absorption or transmittance techniques. Optical sensing typically requires a disposable apparatus and a reusable instrument. The disposable apparatus includes an optical sensor for sensing the blood parameter of interest. The optical sensor is responsive to an optical input signal to provide an optical output signal related to the blood parameter of interest.

In order to provide optical coupling between the disposable apparatus and the reusable instrument, it is necessary to optically connect the instrument to the disposable apparatus. This may be accomplished, for example, by coupling an instrument head to the disposable apparatus. It is important that such optical connection be made with minimal, known optical losses and be repeatable when the disposable apparatus is removed and replaced again on the instrument head.

In the past, the instrument head has been pressed tightly against a surface of the disposable apparatus which contains a shallow, open-ended recess. The instrument head contains an optical transmission member in the form of an optical fiber bundle which is then flush with the outer end of this recess. With this construction, the shallow recess in the disposable element defines an air gap which provides a known and reproducible optical throughput.

This construction works very well so long as there is no moisture in the recess. Unfortunately, however, there is a danger that moisture will accumulate in the recess, and if this occurs, the optical coupling loss changes, the blood parameter readings are upset and repeatability is lost. For example, moisture may form in the recess as the result of condensation of vapors during storage of the disposable apparatus or during setup procedures in the operating room. Moisture may get in the recess when the disposable apparatus is removed after calibration and reattached to the instrument head. Also, condensation from cold lines and cold equipment in the operating room can introduce moisture into the recess during use of the disposable apparatus.

SUMMARY OF THE INVENTION

This invention solves these problems by positively excluding moisture from the optical interface between the disposable apparatus and the instrument and by providing more reproducible or repeatable optical coupling when the disposable apparatus is reattached to the instrument head following calibration. Furthermore, to the extent, if any, that moisture may somehow accumulate in the optical interface, the optical signals passing through the interface are essentially immune to the moisture. Consequently, the blood parameter readings are much more reliable.

This invention may be embodied in an apparatus for use in optically sensing at least one compositional blood parameter which includes a supporting structure having a surface and an optical sensor for sensing the compositional blood parameter. The optical sensor is preferably carried by the supporting structure and is responsive to an optical input signal to provide an optical output signal related to the blood parameter of interest.

To exclude moisture, a deformable optical coupling element or deformable seal is carried by the substrate on the surface of the substrate in a position to receive at least one of the signals. The optical coupling element is transmissive to the optical signal which is to pass therethrough.

In use, the deformable optical coupling element is compressively loaded between an end face of an optical transmission member which may comprise one or more optical fibers or rods and the surface of the supporting structure to deform the optical coupling element. Because the optical coupling element is deformable, it can be loaded against both optical surfaces, i.e. the end face of the optical transmission member and the surface of the supporting structure, to exclude moisture from the optical path between the optical transmission member and the surface. The optical coupling element is transmissive to the wavelengths of interest and so provides optical coupling between the transmission member and the supporting structure. In addition, the optical coupling element serves as a seal to exclude liquid from this optical path.

The optical coupling element has a number of features which enhance its performance. For example, the optical coupling element in an undeformed configuration preferably has a shape which will reduce the likelihood that air will be trapped in the optical path as the optical coupling element is deformed. To accomplish this, the optical coupling element preferably has a convex outer surface and may be, for example, generally dome shaped. A symmetrical convex surface, such as a part spherical surface, is preferred but is not essential.

The property of deformability assists in enabling the optical coupling element to exclude both liquids and gases from the optical path. To further enhance this capability, the optical coupling element preferably has a low contact angle. The contact angle is the angle formed between a plane and a straight line intersecting the plane and tangent to the outer surface of a liquid drop of the optical coupling element material on the plane. A contact angle no greater than about 90 degrees is preferred.

Although it is preferred to have the optical coupling element carried by the supporting structure, the more general requirement is that it lie between the optical surfaces to be coupled. Thus, in a broader sense, the optical coupling element could be secured to either or neither of these surfaces. However, if attachment to a surface is desired, then it is preferred to bond the optical coupling element to such surface because this facilitates manufacture.

One material which has a low contact angle, is bondable to a polycarbonate substrate and readily achieves the desired convex configuration is silicone. Also, silicone is bondable to polycarbonate which, in one preferred embodiment is the material of choice for the supporting structure. Finally, silicone is optically transmissive in the wavelength range of interest which, in one preferred embodiment, is in the range of from about 380 nm to about 600 nm.

To minimize losses at the interface, it is desirable to have the index of refraction of the optical coupling element be close to the indices of refraction of the surfaces being optically coupled. For example, in the case of an optical coupling element between a polycarbonate surface and a glass optical transmission member, the index of refraction of the optical coupling element may be, for example, about 1.45 which is near the indices of refraction of 1.58 and 1.52 for polycarbonate and glass, respectively. In addition, an optical coupling element with an index of refraction of about 1.4 makes the optical transmission properties of the optical coupling at the interface essentially independent of any water which may somehow be trapped at the interface because the index of refraction of water is also near 1.4.

The features of this invention can be utilized in a variety of different apparatuses for use in optically sensing a compositional blood parameter. In one such apparatus, the supporting structure includes a substrate having opposite first and second faces and the optical coupling element is carried by the first face and the optical sensor is carried by the second face. The supporting structure may also include a flow through housing having a flow through passage with an inlet and an outlet. In this event, the optical sensor and the optical coupling element are carried by the housing.

The invention, together with additional features and advantages thereof may best be understood by reference to the following description taken in connection with the accompanying illustrative drawings.

BRIEF DESCRIPTION OF THE DRAWINGS

FIG. 3 is an enlarged fragmentary sectional view taken generally along lines 3—3 of FIG. 1 with the instrument head being optically decoupled from the optical sensor.

FIG. 4 is a sectional view similar to FIG. 3 with the instrument head optically coupled to the optical sensor.

FIG. 5 is an enlarged, fragmentary, sectional view showing a portion of FIG. 2.

FIG. 6 is an enlarged, fragmentary, sectional view showing the instrument head and optical sensor optically decoupled.

FIG. 7 is a sectional view similar to FIG. 6 with the optical sensor and instrument head optically coupled.

DESCRIPTION OF THE PREFERRED EMBODIMENT

Figure 1:
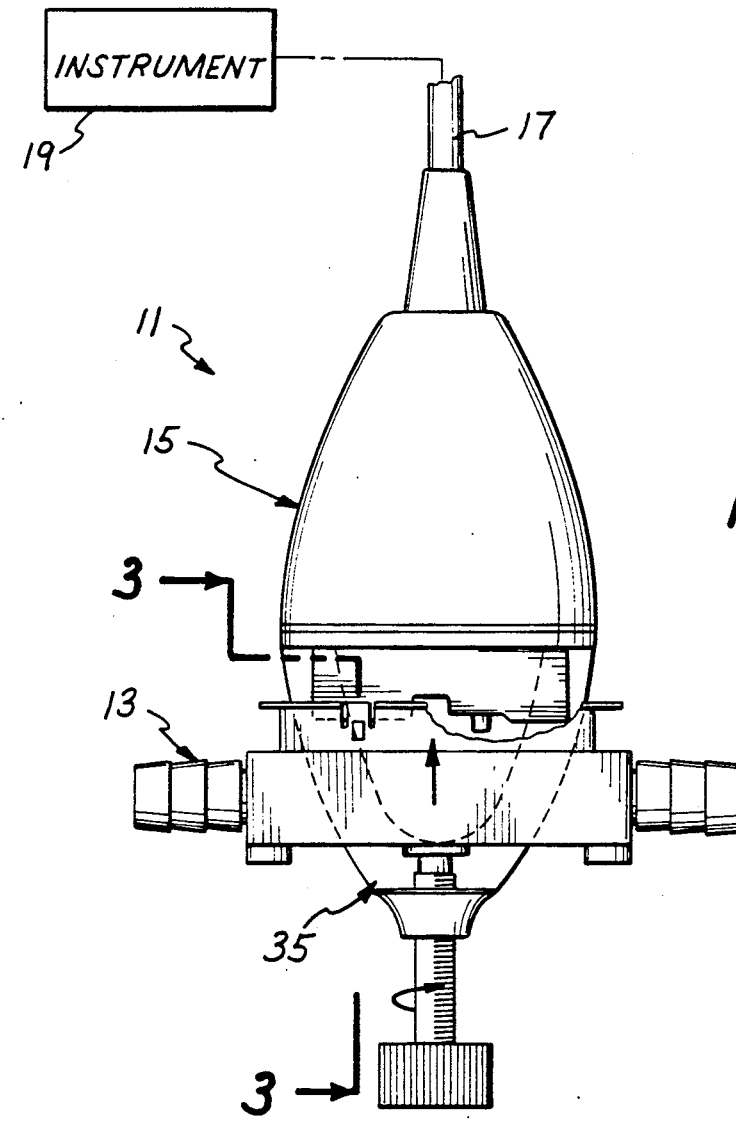
FIG. 1 is a side elevational view of one preferred form of an assembly for use in optically sensing at least one compositional blood parameter constructed in accordance with the teachings of this invention.

FIG. 1 shows an assembly 11 which generally includes a supporting structure in the form of a flow through housing 13 and an instrument head 15 releasably coupled to the flow through housing. A cable 17 couples the instrument head 15 to a conventional instrument 19. The instrument 19 includes a light source for providing an optical input signal and the necessary conventional optics, electronics and software to receive optical output signals related to compositional blood parameters and to provide readings indicating the quantitative values of such compositional blood parameters.

Figure 2:
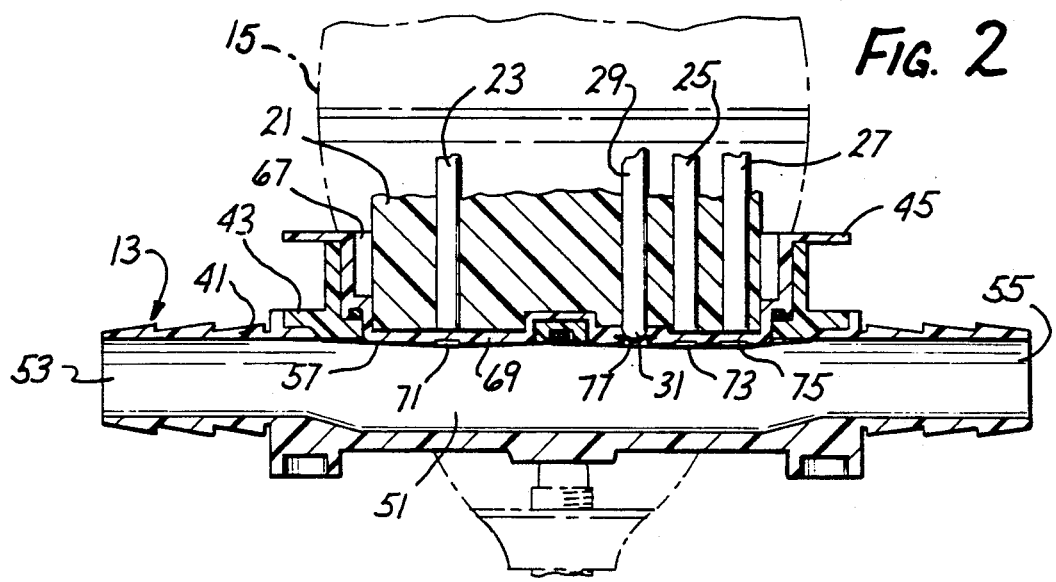
FIG. 2 is a fragmentary axial sectional view through the assembly of FIG. 1.

Although the instrument head 15 can be of various different constructions, in the embodiment illustrated, it includes a molded plastic body 21 (FIG. 2) having optical transmission members in the form of optical fiber bundles 23, 25 and 27 and conductors 29 extending therethrough. A thermistor 31 is carried by the body 21 at one end of the conductors 29. As best seen in FIG. 5, the body 21 terminates in an end surface 33 and the fiber bundles 23, 25 and 27 terminate in end faces 34 which are flush with the end surface 33. The fiber bundles 23, 25 and 27 and the conductors 29 extend through, and form a portion of, the cable 17.

The instrument head 15 also includes a clamp 35 (FIGS. 1, 3 and 4) which comprises a generally C-shaped arm 37 and a screw 39 threadedly attached to the arm.

The flow through housing 13 is only one example of the ways in which this invention can be carried out, and the particular flow through housing illustrated is purely illustrative. The flow through housing 13 is very similar to the flow through housing shown in Cooper U.S. Pat. No. 4,640,820, and the disclosure of the Cooper patent is incorporated by reference herein.

The flow through housing 13 generally comprises a housing section 41, a membrane support 43 and a sensor support 45 (FIGS. 2-5). The membrane support 43 is adhered to the housing section 41 and the sensor support 45 is received within the membrane support and attached thereto by lugs 47 (FIGS. 3 and 4) which are received in apertures 49 of the membrane support. When so assembled, the flow through housing 13 has a flow through passage 51 with an inlet 53 and an outlet 55.

A semi-permeable membrane 57 is carried by the membrane support 43 and extends along the flow through passage 51. Although the membrane 57 may be a single membrane, in the embodiment illustrated, it comprises two membrane sections 59 and 61. The adjacent ends of the membrane sections 59 and 61 are attached to the membrane support 43 in any suitable manner, such as by wrapping them around a retaining bar 63 (FIG. 5) and forcing the retaining bar with the membranes wrapped around it into a groove 65 in the membrane support to mechanically lock the end portions of the membrane sections to the membrane support. This attachment technique is described more fully in Cooper U.S. Pat. No. 4,640,820, which is referred to above. All other peripheral regions of the membrane sections 59 and 61 may be adhered to the membrane support 43 as described in the Cooper patent.

The sensor support 45 defines a cavity or recess 67 which opens upwardly as viewed in FIGS. 3 and 4 and which terminates in a base 69. Optical sensors 71, 73 and 75 and a thermistor receiver 77 are carried by the base 69. The sensors 71, 73 and 75 are selected to sense a compositional blood parameter in the passage 51. Although various different compositional blood parameters can be sensed, in this embodiment of the invention, the sensor 71 senses the partial pressure of oxygen, the sensor 73 senses hydrogen ion concentration or pH and the sensor 75 senses the partial pressure of carbon dioxide. Although optical sensing can be accomplished in different ways, in this embodiment, it is accomplished using fluorescent techniques, and so the sensors 71, 73 and 75 are fluorescent sensors.

The sensors 71, 73 and 75 are adhered to the base 69 using conventional techniques. Thus, the base 69, which serves in effect as a substrate, has opposite faces or surfaces 79 and 81 (FIGS. 5-7) and the sensors 71, 73 and 75 are carried on the face 79. To enable the sensors 71, 73 and 75 to receive and emit light through the base 69, at least regions of the base 69 adjacent the sensors are optically transmissive to the wavelengths of interest. In a preferred construction, the housing section 41, the membrane support 43 and the sensor support 45 are all constructed of clear polycarbonate, although other materials can be used if desired.

Deformable optical coupling elements 83 are carried by the base 69 on the surface 81 in alignment with the sensors 71, 73 and 75, respectively. The coupling elements 83 may be identical, and the coupling element 83 associated with the sensor 71 is shown in an undeformed condition in FIG. 6. The coupling element 83 has a convex outer surface 85 which is dome shaped and in this embodiment is part spherical.

Each of the coupling elements 83 is preferably constructed of a suitable polymer which is applied to the surface 81 in the form of a drop of the polymer in a liquid phase. The polymer is then cured to form the coupling elements 83. As a consequence, each of the coupling elements 83 is bonded to the surface 81.

The configuration of the outer surface 85 is essentially the same in the liquid phase as it is in the cured or solid phase shown in FIG. 6. Accordingly, the optical coupling angle of the coupling element 83 can be illustrated in FIG. 6 even though the coupling element as shown in FIG. 6 is in the solid phase. Thus, the optical coupling element 83 has a contact angle 87 formed between a reference line 89 tangent to the outer surface 85 and intersecting the face 81. The contact angle is preferably no greater than 90 degrees, and in this embodiment is about 20 degrees.

It is desirable to bond the coupling element 83 to the surface 81 and so the material of the coupling element should allow bonding to the material of the base 69. The coupling elements should also be optically clear to whatever optical signal or signals are to be transmitted through them. One material meeting all of these requirements is silicone. A specific kind of silicone that is preferred is dimethylsilicone. One other suitable material is methylphenylsilicone.

In use of the assembly 11, the components are moved from the position shown in FIG. 3 to the position shown in FIG. 4. For this purpose, a portion of the instrument head 15 is sized to be received within the recess 67 and firmly retained therein by the clamp 35. When positioned as shown in FIG. 4, the coupling elements 83 engage and are between the end faces 34, respectively, of the optical fiber bundles 23, 25 and 27 and the surface 81 of the base 69. With reference to FIG. 7, the optical coupling element 83 is compressibly loaded between the end face 34 of the fiber 23 and the surface 81 of the base 69 to deform the optical element from the configuration shown in FIG. 6 generally to the flattened configuration of FIG. 7. Because the coupling element 83 is deformable, by loading it axially, the material of coupling element flows radially over the full area of the end face 34. Accordingly, an optical input signal from the instrument 19 can be transmitted along the optical fiber bundle 23 and through the coupling element 83 and the base 69 to the optical sensor 71. Similarly, a fluorescent optical output signal emitted by the sensor 71 can be transmitted back through the base 69, the coupling element 83 and the optical fiber bundle 23 to the instrument 19 for signal processing.

The coupling element 83 not only optically couples the optical fiber bundle 23 to the base 69 and hence to the sensor 71, but also serves as a seal to exclude liquids and gases from the optical path between the end face 34 and the surface 81. For example, if condensation has formed on the outer surface 85 of the coupling element 83 prior to assembling the instrument head 15 into the cavity 67, this moisture will be squeezed radially outwardly and out of the optical path between the optical fiber bundle 23 and the coupling element 83. Furthermore, if a liquid should somehow enter the space between the end surface 33 of the body 21 and the surface 81, the deformed coupling element 83 acts as a seal to exclude this liquid from the optical path.

It is also important to exclude air from the optical path as the coupling element 83 is being deformed radially outwardly. This air exclusion function, and well as the liquid exclusion function, is enhanced by the convex shape of the outer surface 85 which tends to force both liquids and gases radially outwardly as the axial dimension of the coupling element is reduced because of the compressive forces. The low contact angle 87 reduces the likelihood that tiny microcompartments of air or liquid will be trapped between the end face 34 and the outer surface 85 as the coupling element 83 is being axially compressed toward the position shown in FIG. 7. All of the optical coupling elements 83 function as described above to provide both optical coupling and liquid and gas exclusion from their respective optical paths.

The sensors 71, 73 and 75 can be placed in the presence of compositional blood parameters in various ways. However, in the embodiment illustrated, the flow through passage 51 is coupled into an extracorporeal blood path such as occurs in open heart surgery so that the flow through passage 51 forms a part of the extracorporeal loop. Accordingly, blood flows along the membrane sections 59 and 61. The membrane sections 59 and 61 are semi-permeable and pass the blood component of interest and serve as barriers for the other components of the blood. Thus, the membrane section 59 passes oxygen to the optical sensor 71 and the membrane section 61 passes hydrogen ions and dissolved carbon dioxide to the optical sensors 73 and 75. Each of the sensors 71, 73 and 75 contains a fluorescent indicator which, when excited by an optical input signal from the instrument 17, emits a fluorescent optical output signal of a different wavelength than the input signal. The output signals can be correlated by the instrument 19 to provide quantitative readings for the compositional blood parameters of interest. Although many different arrangements are possible, in this embodiment the exciting light or the optical input signal has a wavelength in the range of from about 380 nm to about 470 nm and the optical output signals have a wavelength in the range of from about 500 nm to about 600 nm.

Although an exemplary embodiment of the invention has been shown and described, many changes, modifications, and substitutions may be made by one having ordinary skill in the art without necessarily departing from the spirit and scope of the invention.

I claim:

1. An assembly for use in optically sensing at least one compositional blood parameter comprising:
   a supporting structure having a surface;

an optical sensor for sensing the compositional blood parameter, said optical sensor being carried by the supporting structure and being subject to the compositional blood parameter, said optical sensor being responsive to an optical input signal to provide an optical output signal related to said compositional blood parameter;

an elongated optical transmission member including at least one optical fiber having an end face confronting said surface of the supporting structure;

a deformable optical coupling element attached to said surface of the supporting structure and releasably engaging said end face of said optical fiber, said optical coupling element being compressively loaded between said surface sand said end face of said optical fiber to deform the optical coupling element whereby an optical path is provided through the optical coupling;

said optical coupling element being in a position to receive at least one of said signals and said optical coupling element being transmissive to at least one of said signals; and said optical transmission member being separable from the surface and said optical coupling element to expose said end face of said fiber.

2. An assembly defined in claim 1 wherein said optical coupling element has a contact angle no greater than about 90 degrees.

3. An assembly as defined in claim 1 wherein said optical coupling element is constructed of silicone.

4. An assembly as defined in claim 1 wherein said optical coupling element is transmissive to light in the range of from about 380 nm to about 600 nm.

5. An assembly as defined in claim 1 wherein the optical coupling element in an undeformed configuration has a convex outer surface.

6. An assembly as defined in claim 1 wherein the optical coupling element in an undeformed configuration has a generally dome-shaped configuration.

7. An assembly as defined in claim 1 wherein the supporting structure includes a substrate having opposite first and second faces, said surface includes said first face and said optical coupling element is bonded to said first face.

8. An assembly as defined in claim 7 wherein the optical coupling element in an undeformed configuration has a generally dome-shaped configuration.

9. An assembly as defined in claim 7 wherein the index of refraction of the optical coupling element is near the indices of refraction of the optical transmission member and the substrate.

10. An assembly as defined in claim 1 wherein the supporting structure includes a flow through housing having a flow through passage with an inlet and an outlet and said optical sensor and optical coupling element are carried by the housing.

11. An assembly as defined in claim 10 including a membrane carried by the housing and separating the sensor from the passage, said membrane being permeable to said compositional blood parameter.

12. An assembly for use in optically sensing at least one compositional blood parameter comprising:

a substrate having opposite first and second faces;

an optical sensor for sensing the compositional blood parameter, said optical sensor being positioned on the second face of said substrate and being subject to the compositional blood parameter, said optical sensor being responsive to an optical input signal to provide an optical output signal related to said compositional blood parameter;

a deformable optical coupling element attached to the first face of said substrate in a position to receive at least one of said signals, and said optical coupling element and said substrate being transmissive to said one signal;

a head including a body having an end surface and at lest one optical fiber carried by the body and having an end face;

said head being releasably coupled to the substrate such that said deformable optical coupling element releasably contacts said end face of the optical fiber so as to form an uninterrupted optical path from the optical fiber, through said optical coupling element, through said substrate, and to said optical sensor; and said head being separable from the substrate to expose said end face of said fiber.

13. An assembly as defined in claim 12 wherein said end face is flush with said end surface.

14. An assembly as defined in claim 12 wherein said optical coupling element has a convex outer surface.

15. An assembly as defined in claim 12 wherein said optical coupling element is generally dome shaped.

16. An assembly as defined in claim 12 wherein said optical coupling element is constructed of silicone.

17. An assembly as defined in claim 12 wherein said optical coupling element has a convex outer surface, is constructed of silicone and is bonded to said first face.

18. An assembly as defined in claim 12 wherein said optical coupling element is transmissive to light in the range of from about 380 nm to about 600 nm.

19. An assembly as defined in claim 12 further comprising a the supporting structure which includes a said substrate and further includes a flow through housing having a flow through passage with an inlet and an outlet, and said optical sensor and optical coupling element being carried by the housing.

20. An assembly as defined in claim 19 including a membrane carried by the housing and separating the sensor from the passage, said membrane being permeable to said compositional blood parameter.

21. An assembly for use in optically sensing at least one compositional blood parameter comprising:

a substrate having opposite first and second faces;

an optical sensor for sensing the compositional blood parameter, said optical sensor being positioned on the second face of said substrate and being subject to the compositional blood parameter, said optical sensor being responsive to an optical input signal to provide an optical output signal related to said compositional blood parameter;

a deformable optical coupling element attached to the first face of said substrate in a position to receive at least one of said signals, and said optical coupling element and said substrate being transmissive to said one signal;

a head including a body having an end surface and an optical transmission member carried by the body and having an end face flush with the end surface;

said head being releasably couplable to the substrate such that the deformable optical coupling element releasably contacts said end face of the optical transmission member to form an uninterrupted optical path from the optical transmission member through said optical coupling element, through said substrate, and to said optical sensor; and said head being separable from the substrate to expose said end face of said optical transmission member.

* * * * *

UNITED STATES PATENT AND TRADEMARK OFFICE
CERTIFICATE OF CORRECTION

PATENT NO. : 5,104,623

DATED : April 14, 1992

INVENTOR(S) : William W. Miller

It is certified that error appears in the above-identified patent and that said Letters Patent is hereby corrected as shown below:

Col. 7, line 15, "sand" should be --and--

Col. 7, line 26, before "defined" insert --as--

Col. 8, line 9, "lest" should be --least--

Col. 8, line 33 in claim 19, line 2, delete "the"

Col. 8, line 33 in claim 19, line 2, delete the second occurrence of "a"

Signed and Sealed this

Third Day of August, 1993

*Attest:*

MICHAEL K. KIRK

*Attesting Officer*  *Acting Commissioner of Patents and Trademarks*